United States Patent [19]

Kani et al.

[11] 4,256,384

[45] Mar. 17, 1981

[54] EYEBALL EXAMINING DEVICE

[75] Inventors: Kazutaka Kani; Kuniomi Abe; Masahiko Konagaya, all of Kobe; Noboru Ono, Nishinomiya, all of Japan

[73] Assignee: Konan Camera Research Institute, Hyogo, Japan

[21] Appl. No.: 85,002

[22] Filed: Oct. 15, 1979

[51] Int. Cl.³ .......................... A61B 3/14; A61B 3/10; G03B 29/00
[52] U.S. Cl. ........................................ 351/7; 351/13; 354/62
[58] Field of Search .......................... 351/6, 7, 13, 16; 354/62

[56] References Cited

U.S. PATENT DOCUMENTS 4,149,787  4/1979  Kobayashi .......................... 351/7 X Primary Examiner—John K. Corbin
Assistant Examiner—Rodney Bovernick
Attorney, Agent, or Firm—Eugene E. Geoffrey, Jr.

[57] ABSTRACT

An eye examining device having a television camera and monitor connected thereto, an optical system for magnifying the eye ground or retina and focussing the image on the camera, a cathode ray tube connected with the camera and scanned in synchronism therewith, a light pattern generator connected with the cathode ray tube and monitor for display thereof and an optical system for projecting the image on the cathode ray tube onto the eye ground.

3 Claims, 1 Drawing Figure

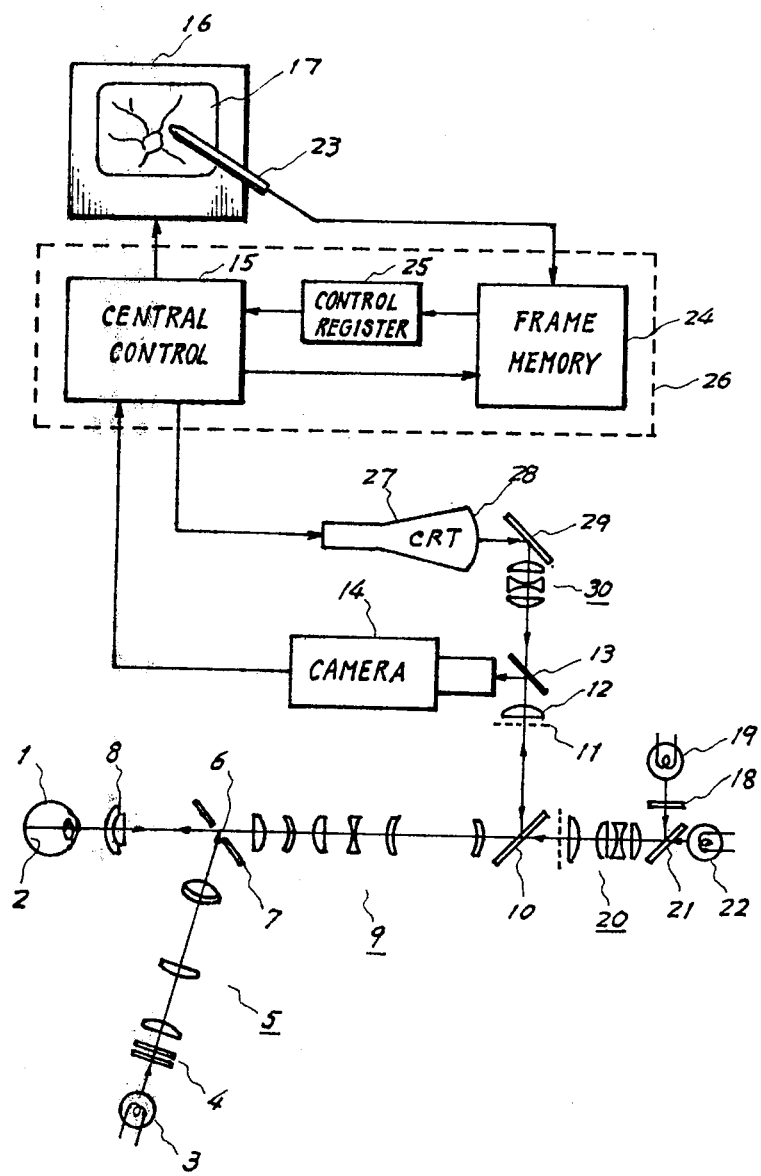

EYEBALL EXAMINING DEVICE

This invention relates to an eyeball examining device and more specifically a device for examining eye functions such as light sensitivity distribution over the eye ground or retina and eyeball motion by projecting a visible light beam onto various areas of the eye ground while observing a magnified image of the eye ground on an infrared ray television monitor.

Although such devices have been known as eye ground visual field testers or eyeball motion testers, it has been difficult to provide accurate correspondence of the magnified image with the area illuminated by the visible light beam. More particularly, it has been difficult to direct a visible light beam onto a small specific area of the eye ground which is designated in the eye ground image displayed on the monitor or, contrarily, to specify in the displayed eye ground image the area which is now illuminated by a visible light beam.

Accordingly, an object of this invention is to provide an eyeball examining device which can rapidly and accurately direct a light beam onto any area of the eye ground by designating a corresponding area in a magnified monitoring image.

Another object of this invention is to provide such a device which can also project an optical pattern other than a light spot onto the eye ground and, at the same time, display the same pattern in superposition with the eye ground image displayed on the monitor.

According to the principle of this invention, the device comprises a television pick-up camera, a main optical system for magnifying an eye ground image and coupling it to the television camera, an infrared ray source, means for directing an infrared ray beam from this source to the eye ground through a part of the main optical system and a television monitor for displaying the image picked up by the television camera. This invention further comprises a cathode ray tube having a display screen which is scanned in synchronism with the scan of the television camera, means for generating a light pattern and displaying it on the cathode ray tube and the television monitor, and means for projecting the displayed image of the cathode ray tube onto the eye ground through the main optical system.

These and other objects and features of this invention will be described in more detail hereinunder with reference to the accompanying drawing.

IN THE DRAWING

The single drawing shows an embodiment of the device according to this invention.

In the drawing, an eye 1 having an eye ground or retina 2 to be examined is illuminated by a light source 3. The light from the light source 3 is filtered by an infrared ray filter 4 which allows only infrared rays to pass therethrough and the filtered infrared rays are directed onto the eye 1 through condenser lenses 5, mirror 7 having central hole 6, and microscope objective 8 to illuminate the eye ground 2. The infrared rays reflected by the eye ground 2 are led through the objective 8, the central hole 6 of the mirror 7, imaging lenses 9 and half-mirror 10 to form an infrared ray image 11 of the eye ground 2. This image 11 is picked up through an intermediate lens 12 and a half-mirror 13 by a television camera 14. The video signal from the camera 14 is processed in a central control unit 15 and visibly displayed on the screen 17 of a television monitor 16 as a magnified image.

The device also includes a fixed reference mark 18 which is illuminated by a visible light source 19. This mark is used for enabling the eye 1 to properly face to the device by looking hard at it through the objective 8, central hole 6, imaging lenses 9, half-mirror 10, imaging lenses 20 and a half-mirror 21. Another light source 22 is provided for projecting a weak visible light onto the whole range of the eye ground 2 through the half-mirror 21, imaging lenses 20, half-mirror 10, imaging lenses 9, central hole 6 and objective 8 to provide a background with suitable brightness.

The arrangement as described above is common to known eye ground visual field testers according to the prior art, except for some differences in light path arrangement. In such prior art devices, a visible light beam is introduced from the outside into the above mentioned light path to project a light spot onto the eye ground 2. The examiner may change the position, brightness, size and the like of the light spot while adjusting brightness of the background light source 22 and inquire of the examinee about whether he can see the light spot or not, thereby measuring sensitivities of various areas of the eye ground 2. However, the light spot could not be displayed clearly on the screen 17 of the monitor 16 and, therefore, it was difficult to obtain an accurate position of the light spot on the displayed image.

In the preferred embodiment of this invention, a known light pen system and a cathode ray tube are utilized for projecting a light spot onto the eye ground 2. The light pen system includes a light pen 23 having a photosensitive element at the tip, which senses a light emitted from a specific small area of the screen 17 to which the tip is put into contact and produces a detection output. This output from the light pen 23 is coupled to a frame memory 24 which is included in a computer 26 together with a control register 25 and the central control unit 15. Memory locations of the frame memory 24 are scanned in synchronism with the monitor 16 under control of the central control unit 15 and the output of the light pen 23 is written in the location corresponding to the specific area of the screen 17. The stored signal is read out through the control register 25 to the central control unit 15 and displayed as a bright spot on the monitor screen 17 and at the same time on a screen 28 of a cathode ray tube 27 which is scanned in synchronism with the monitor 16 under control of the central control unit 15. It will be understood that accurate positional coincidence is obtained between both displayed spots. The spot displayed on the cathode ray tube screen 28 is imaged on the image plane 11 of the eye ground through mirror 29, imaging lenses 30, half-mirror 13 and intermediate lens 12 and then projected on to the eye ground 2 through the main optical path of the device. The imaging position of the spot on the eye ground corresponds to the position of the displayed spot on the monitor screen 17.

The control register 25 is used for controlling the diameter of the bright spot displayed. Brightness of the spot can be controlled arbitrarily by adjusting the conventional luminance modulation circuit (not shown) of the cathode ray tube 27.

The device can also be utilized as an eyeball motion tester, when the light source 19 is turned off and the bright spot is moved adequately. The examiner may have the examinee look hard at the moving spot and examine the motion of the eye ground following it.

While, in the illustrated embodiment, a bright spot was displayed on the cathode ray tube screen 28 by utilizing a light pen system, this invention is not limited to this configuration. The range of an eyeball examination can be widened by displaying a suitable test pattern on the cathode ray tube. This can be effected by providing a suitable pattern generator which is known in the art, in the central control unit 15 and supplying a video signal corresponding to a suitable pattern to the cathode ray tube 27 and the monitor 16. For example, a frequency characteristic examination can be done with a striped pattern and vision test can be effected at any position of the eye ground by using a vision test chart. Furthermore, a colored pattern can be displayed as occasion demands, if a color cathode ray tube is used. Moreover, it is possible to provide a function of haploscope which can examine the both eyes at the same time to effect examination of strabism and amblyopia, when a pair of such devices are provided.

What is claimed is:

1. An eyeball examining device, comprising a television pick-up camera, a main optical system for coupling an eye ground image to said television camera, an infrared ray source, means for directing infrared rays from said source to the eye ground, and a television monitor for displaying the image picked up by said television camera, said device further comprising a cathode ray tube scanned in synchronism with said television monitor, means for generating an image signal and coupling it to said television monitor and cathode ray tube, and an optical system for introducing the displayed image of said cathode ray tube into said main optical system to project it upon the eye ground.

2. An eyeball examining device according to claim 1 wherein said image signal generating means includes a pattern generator.

3. An eyeball examining device according to claim 1 wherein said image signal generating means includes a light sensitive pen, a frame memory having memory locations scanned in synchronism with said television monitor for storing the output of said light pen, and control means for coupling the signal read out of said frame memory to said television monitor and cathode ray tube.

* * * * *